United States Patent
Tracey et al.

(10) Patent No.: US 12,109,255 B2
(45) Date of Patent: Oct. 8, 2024

(54) CHOLINE ACETYLTRANSFERASE AS A THERAPY FOR HYPERTENSION

(71) Applicant: THE FEINSTEIN INSTITUTES FOR MEDICAL RESEARCH, Manhasset, NY (US)

(72) Inventors: Kevin J. Tracey, Old Greenwich, CT (US); Sangeeta S. Chavan, Syosset, NY (US); Andrew Stiegler, Deer Park, NY (US); Jian Hua Li, New York, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 631 days.

(21) Appl. No.: 17/299,392

(22) PCT Filed: Dec. 11, 2019

(86) PCT No.: PCT/US2019/065653
§ 371 (c)(1),
(2) Date: Jun. 3, 2021

(87) PCT Pub. No.: WO2020/123611
PCT Pub. Date: Jun. 18, 2020

(65) Prior Publication Data
US 2022/0054599 A1  Feb. 24, 2022

Related U.S. Application Data

(60) Provisional application No. 62/778,355, filed on Dec. 12, 2018.

(51) Int. Cl.
| A61K 38/45 | (2006.01) |
| A61K 47/60 | (2017.01) |
| A61P 9/12  | (2006.01) |

(52) U.S. Cl.
CPC .............. *A61K 38/45* (2013.01); *A61K 47/60* (2017.08); *A61P 9/12* (2018.01); *C12Y 203/01006* (2013.01)

(58) Field of Classification Search
CPC ...... A61K 38/45; A61K 47/60; A61K 9/0019; A61P 9/12; C12Y 203/01006
See application file for complete search history.

(56) References Cited

U.S. PATENT DOCUMENTS 6,656,743 B2   12/2003   Huson et al.
11,298,408 B2   4/2022   Hanes et al.

FOREIGN PATENT DOCUMENTS

WO   2018049095 A1   3/2018

OTHER PUBLICATIONS

Olofsson, Peder S., et al. "Blood pressure regulation by CD4+ lymphocytes expressing choline acetyltransferase." Nature biotechnology 34.10 (2016): 1066-1071. doi: 10.1038/nbt.3663. (Year: 2016).*
Charles L, Triscott J, Dobbs B. Secondary Hypertension: Discovering the Underlying Cause. Am Fam Physician. Oct. 1, 2017;96(7): 453-461. PMID: 29094913. (Year: 2017).*
Bremer U, Horres CR, Francoeur ML. Protein delivery with infusion pumps. Pharm Biotechnol. 1997;10:239-54. doi: 10.1007/0-306-46803-4_9. PMID: 9160375. pp. 239-240 Only. (Year: 1997).*
NCBI Blast search result for choline acetyltransferase isoform R, human CHAT protein, GenBank AI30616.1 retrieved on Apr. 1, 2024 from NCBI, 2 pages of PDF. (Year: 2024).*
Olofsson P et al., "Choline acetyltransferase+ lymphocytes regulate endothelial nitric oxide synthase (MUC2P.939)," J Immunol, May 1, 2015, 194 (1 Supplement) 65.22; pp. 1-2.
Moore T V et al., "Relationship between CD8-dependent antigen recognition, T cell functional avidity, and tumor cell recognition," Cancer Immunol Immunother (2009) 58:719-728.
Peder S. Olofsson et al., "Blood pressure regulation by CD4 + lymphocytes expressing choline acetyltransferase," Nature Biotechnology, vol. 34, No. 10, Oct. 2016, pp. 1066-1071, XP055904501, ISSN: 1087-0156, doi: 10.1038/nbt.3663.
Ae-Ri Kim et al., "Two methods for large-scale purification of recombinant human choline acetyltransferase," Protein Expression and Purification, vol. 40, No. 1, Mar. 2005, pp. 107-117, XP004753568, ISSN: 1046-5928, doi: 10.1016/j.pep.2004.12.011.
Ai Ling Fu et al., "Alternative therapy of Alzheimer's disease via supplementation with choline acetyltransferase," Neuroscience Letters, vol. 368, No. 3, Sep. 30, 2004, pp. 258-262, XP004567921, ISSN: 0304-3940, doi: 10.1016/j.neulet.2004.05.116.
European Patent Office, "Partial Supplementary European Search Report," issued in European Patent Application No. 19 894 449.8, which is a counterpart to U.S. Appl. No. 17/299,392, issued on May 3, 2022, 20 pages.
European Patent Office, "Extended European Search Report," issued in European Patent Application No. 19 894 449.8, which is a counterpart to U.S. Appl. No. 17/299,392, issued on Jul. 1, 2022, 23 pages.
Francesco M Veronese et al., "The impact of PEGylation on Biological Therapies," BioDrugs, vol. 22, No. 5, 2008, pp. 315-329. doi: 10.2165/00063030-200822050-00004, XP009116032.
Thermo Scientific, "MS(PEG)12 Methyl-PEG-NHS-Ester Reagent," ThermoFisher Scientific, Catalog No. 22685, [online] https://web.archive.org/web/20180526055643/https://www.thermofisher.com/order/catalog/product/22685.
Diaferia C et al, "Structural Characterization of PEGylated Hexaphenylalanine Nanostructures Exhibiting Green Photoluminescence Emission," Chemistry. Oct. 9, 2017, Epub Sep. 12, 2017. vol. 23, No. 56; pp. 14039-14048.

(Continued)

*Primary Examiner* — Kade Ariani
(74) *Attorney, Agent, or Firm* — Amster, Rothstein & Ebenstein LLP

(57) ABSTRACT

Compositions and methods are provided comprising choline acetyltransferase (ChAT) and PEGylated ChAT for treating hypertension.

18 Claims, 8 Drawing Sheets

Specification includes a Sequence Listing.

(56) References Cited

OTHER PUBLICATIONS

PCT International Search Report dated Feb. 27, 2020 in connection with PCT/US2019/065653.

PCT Written Opinion of the International Searching Authority Report dated Feb. 27, 2020 in connection with PCT/US2019/065653.

Takeshi Fujii et al., "Species differences in the concentration of acetylcholine, a neurotransmitter, in whole blood and plasma", Neuroscience Letters, vol. 201, Issue 3, Dec. 1995, pp. 207-210, Elsevier Science Ireland Ltd.

Swetha Vijayaraghavan et al., "Regulated Extracellular Choline Acetyltransferase Activity—the Plausible Missing Link of the Distant Action of Acetylcholine in the Cholinergic Anti-Inflammatory Pathway", PLOS One, vol. 8, Issue 6, Jun. 2013, e65936, 15 pages, https://doi.org/10.1371/journal.pone.0065936.

* cited by examiner

CHOLINE ACETYLTRANSFERASE AS A THERAPY FOR HYPERTENSION

CROSS-REFERENCE TO RELATED APPLICATIONS

This application is a U.S. national stage entry under 35 U.S.C. § 371 of PCT International Patent Application No. PCT/US2019/065653, filed Dec. 11, 2019, which claims the benefit of U.S. Provisional Patent Application No. 62/778,355 filed on Dec. 12, 2018, the contents of which are herein incorporated by reference into the subject application.

BACKGROUND OF THE INVENTION

Throughout this application various publications are referred to in parentheses. Full citations for these references may be found at the end of the specification. The disclosures of all publications, patents and patent applications mentioned herein are hereby incorporated by reference in their entirety into the subject application to more fully describe the art to which the subject invention pertains.

Systemic hypertension is a long-term condition in which the blood pressure in the systemic arteries is persistently elevated. Normal blood pressure for most human adults at rest is in the range of 100 to less than 120 millimeters mercury (mmHg) for systolic blood pressure and 60 to less than 80 mmHg for diastolic blood pressure. Hypertension can be defined as resting blood pressure that is persistently at or above 130/80 mmHg (systolic/diastolic). The cause or causes of most cases of hypertension are unknown, i.e., so-called "primary" hypertension. In a minority of cases, so-called "secondary" hypertension, high blood pressure can be attributed to an identifiable cause, such as narrowing of the arteries or chronic kidney disease. Hypertension remains a major risk factor for a variety of diseases including coronary artery disease, stroke, heart failure, atrial fibrillation, peripheral vascular disease, vision loss, chronic kidney disease and dementia.

Choline acetyltransferase (ChAT) is an enzyme that catalyzes the transfer of an acetyl group from the coenzyme, acetyl-Coenzyme-A, to choline, yielding acetylcholine (ACh). Studies have shown the use of ChAT for improving cognitive disorders. Administration of ChAT coupled to protein transduction domain (PTD) improved age-related cognitive defects in aged mice (Fu et al. 2005). Similarly, U.S. Pat. No. 9,248,152 showed that implantation of neural stem cells (NSCs) stably expressing human ChAT improved learning and memory in a rat model and proposed the use of these stem cells for treating Alzheimer's disease as well as cognitive disorders due to other brain diseases and aging. WO 2005/071071 proposed using a PTD-ChAT fusion protein for treating neurodegenerative disease, preventing Alzheimer's disease, and advancing memory and learning. Similarly, U.S. Pat. No. 7,083,930 B2 proposed that ChAT polypeptides may be used to treat amyotrophic lateral sclerosis, Alzheimer's disease, senile dementia, multi-infarct dementia, familial disautonomia, Huntington's disease, mental retardation, memory loss, and myasthenia gravis, as well as disorders known to involve the cholinergic system or affect its pathways and nerves in the body, including for example gut and GI disorders, cord disorders, including movement, continence and sensation, brainstem disorders, including sleep, blood pressure, respiration, and balance, hypothalamus disorders, including temperature, respiration, and endocrine function, and limbic system disorders, including schizophrenia, memory disorders and dementia.

Currently, only roughly one-half of patients with high blood pressure successfully control their blood pressure (CDC Fact Sheet 2016). The present invention addresses the need for treating hypertension by providing the use of ChAT and modified ChAT peptides to treat hypertension.

SUMMARY OF THE INVENTION

The present invention provides methods of reducing hypertension in a subject in need thereof comprising administering to the subject choline acetyltransferase (ChAT) or PEGylated ChAT in an amount and manner effective to reduce hypertension in a subject. Also provided are pharmacological compositions comprising PEGylated ChAT and a pharmaceutically acceptable carrier.

DETAILED DESCRIPTION OF THE INVENTION

Figure 1A:
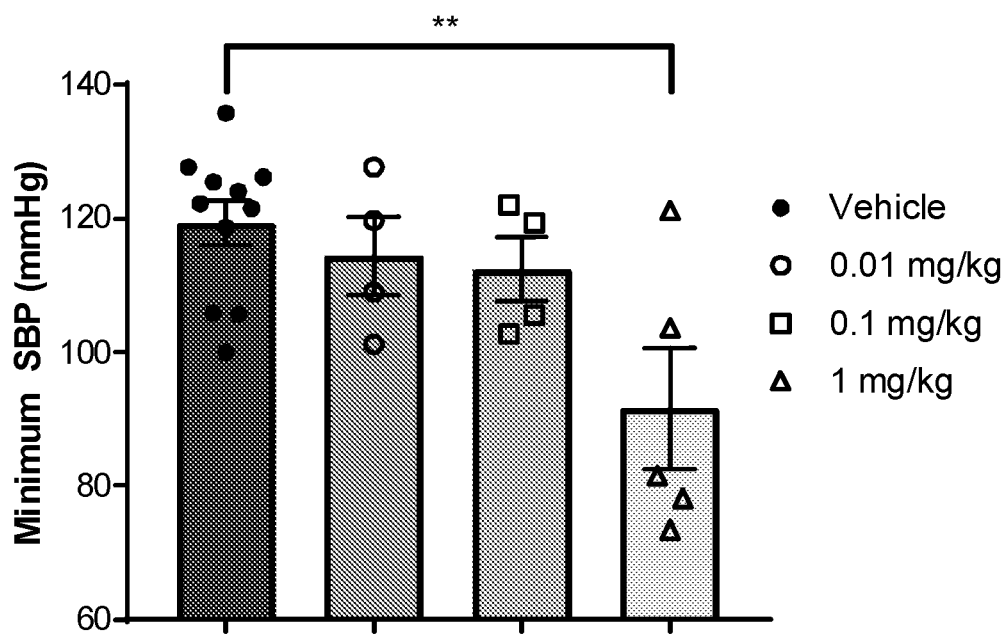
FIG. 1A-1B. Single injection of ChAT decreases systolic blood pressure (SBP) in hypertensive mice. A) Minimum SBP during 12 hour post-injection period. B) Area-under-curve (AUC) of hypertensive-normalized SBP during 12 hour post-injection period. Histograms from left to right in each time period: Vehicle, 0.01 mg/kg, 0.1 mg/kg, 1 m/kg. For 1 mg/kg ChAT group, n=5. For 0.1 mg/kg ChAT and 0.01 mg/kg ChAT groups, n=4. For vehicle group, n=11. **$p<0.01$.

The present invention provides a method of reducing systemic hypertension in a subject in need thereof comprising administering to the subject choline acetyltransferase (ChAT) or ChAT conjugated to polyethylene glycol (PEG) in an amount and manner effective to reduce hypertension in a subject.

Preferably, the ChAT is human ChAT. The ChAT can be a recombinant ChAT. In one embodiment, the ChAT is ChAT isoform R.

The ChAT can be conjugated to polyethylene glycol (PEG). For example, ChAT can be conjugated to 2-24 PEG chains. In one embodiment, ChAT is conjugated to 12 PEG chains. Each PEG chain can have a molecular weight of, for example, 200-2,000 daltons. In one embodiment, PEG-ChAT has a molecular weight about 20,000 daltons greater than ChAT. Conjugation of PEG to ChAT can be effective to increase the solubility and/or half-life of ChAT.

The subject can be any mammal and is preferably a human. In one embodiment, the subject is an adult human 18 years or older who prior to administration of ChAT or PEGylated ChAT had a resting systolic blood pressure at or above 130 mmHg and/or a diastolic blood pressure at or above 80 mmHg. In one embodiment, the subject is an adult human 18 years or older who prior to administration of ChAT or PEGylated ChAT had a resting systolic blood pressure at or above 140 mmHg and/or a diastolic blood pressure at or above 90 mmHg. In one embodiment, the subject has primary hypertension. In one embodiment, the subject has secondary hypertension. In one embodiment, the subject has narrowing of the arteries and/or chronic kidney disease.

In one embodiment, the subject does not have any one or more of an age-related cognitive disorder, Alzheimer's disease, a neurodegenerative disease, amyotrophic lateral sclerosis, senile dementia, multi-infarct dementia, familial disautonomia, Huntington's disease, mental retardation, memory loss, myasthenia gravis, a gastrointestinal tract disorder, a spinal cord disorder, a brainstem disorders, a hypothalamic disorder, a limbic system disorder and dementia.

ChAT or PEGylated ChAT can be administered by any route known to those skilled in the art. In different embodiments, ChAT or PEGylated ChAT is administered by intravenous or intraperitoneal injection or infusion via a device such as an osmotic pump. In one embodiment, ChAT or PEGylated ChAT is administered by injections or infusions spaced over an interval of one or more days.

Preferably, administration of ChAT or PEGylated ChAT is effective to reduce systolic blood pressure by at least 10 mmHg, more preferably by at least 20 mmHg, and most preferably by at least 30 mmHg. In one embodiment, administration of ChAT or PEGylated ChAT is effective to reduce systolic blood pressure by 10-40 mmHg.

Also provided is a pharmacological composition comprising choline acetyltransferase (ChAT) conjugated to polyethylene glycol (PEG) and a pharmaceutically acceptable carrier. For example, ChAT can be conjugated to 2-24 PEG chains. In one embodiment, ChAT is conjugated to 12 PEG chains. Each PEG chain can have a molecular weight of, for example, 200-2,000 daltons. In one embodiment, PEG-ChAT has a molecular weight about 20,000 daltons greater than ChAT. The PEGylated ChAT can be formulated in dosage form for administration to a subject for treatment of hypertension.

Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution.

In an embodiment, human choline acetyltransferase has the following amino acid sequence (GenBank: AAA14245.1; SEQ ID NO:1):

```
  1 mglrtakkrg lggggkwkre egggtrgrre vrpacflqsg grgdpgdvgg pagnpgcsph 61 praatrpppl pahtpahtpe wcgaasaeaa eprragphlc ipapgltktp ilekvprkma 121 aktpsseesg lpklpvpplq qtlatylqcm rhlvseeqfr ksqaivqqfg apgglgetlq 181 qkllerqekt anwvseywln dmylnnrlal pvnsspavif arqhfpgtdd qlrfaaslis 241 gvlsykalld shsiptdcak pelsgqplcm kqyyglfssy rlpghtqdtl vaqnssimpe 301 pehvivacon qffvldvvin frrlsegdlf tqlrkivkma snederlppi glltsdgrse 361 waeartvlvk dstnrdsldm ierciclvcl dgpggvelsd thralqllhg ggysknganr 421 wydkslqfvv grdatcgvvc ehspfdgivl vqctehllkh mtqssrklir adsvselpap 481 rrlrwkcspe iqghlassae klqriviknld fivykfdnyg ktfikkqkcs pdafiqvalq 541 lafyrlhrrl vptyesasir rfqegrvdni rsatpealaf vravtdhkaa vpasekllll 601 kdairaqtay tvmaitgmai dnhllalrel aramckelpe mfmdetylms nrfvlstsqv
```

-continued

```
661 ptttemfccy gpvvpngyga cynpqpetil fcissfhsck etssskfaka veeslidmrd 721 lcsllpptes kplatkekat rpsqghqp.
```

In an embodiment, human choline acetyltransferase isoform R has the following amino acid sequence (GenBank: AAK08955.1; SEQ ID NO:2):

```
  1 maaktpssee sglpklpvpp lqqtlatylq cmrhlvseeq frksqaivqq fgapgglget 61 lqqkllerqe ktanwvseyw lndmylnnrl alpvnsspav ifarqhfpgt ddqlrfaasl 121 isgvlsykal ldshsiptdc akgqlsgqpl cmkqyyglfs syrlpghtqd tlvaqnssim 181 pepehvivac cnqffvldvv infrrlsegd lftqlrkivk masnederlp piglltsdgr 241 sewaeartvl vkdstnrdsl dmierciclv cldapggvel sdthralqll hgggysknga 301 nrwydkslqf vvgrdgtcgv vcehspfdgi vlvqctehll khmtqssrkl iradsvselp 361 aprilrwkcs peiqghlass aeklqrivkn ldfivykfdn ygktfikkqk cspdafiqva 421 lqlafyrlhr rlvptyesas irrfqegrvd nirsatpeal afvravtdhk aavpasekll 481 llkdairaqt aytvmaitgm aidnhllalr elaramckel pemfmdetyl msnrfvlsts 541 qvptttemfc cygpvvpngy gacynpqpet ilfcissfhs cketssskfa kaveeslidm 601 rdlcsllppt eskplatkek atrpsqghqp.
```

"And/or" as used herein, for example, with option A and/or option B, encompasses the separate embodiments of (i) option A, (ii) option B, and (iii) option A plus option B.

Where a numerical range is provided herein, it is understood that all numerical subsets of that range, and all the individual integers contained therein, are provided as part of the invention.

All combinations of the various elements described herein, including all subsets, are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Methods and Materials

Animals. Male C57BL/6 mice were obtained from Jackson Laboratories (Bar Harbor, ME) at 12 weeks of age. All mice were maintained in temperature-controlled rooms on a 12 h light-dark cycle with access to food and water ad libitum. Mice were singly housed after implanting blood pressure telemeters. All experimental protocols were approved by the Institutional Animal Care and Use Committee (IACUC) at the Feinstein Institutes for Medical Research (FIMR), Northwell Health, which follows the NIH guidelines for ethical treatment of animals.

Blood pressure measurements. Mice were induced under 2.5% isoflurane and implanted with HD-X10 blood pressure telemeters (DSI, New Brighton MN). A catheter was placed in the left carotid artery and advanced to the aortic arch. The telemeter body was placed in a subcutaneous pocket on the animal's flank, and blood pressure measurements were taken after an intervening period of 7 days.

Angiotensin II administration. Angiotensin II human (ThermoFisher) was purchased. Osmotic pumps (Alzet model 1004, Cupertino CA, 95014) were loaded with angiotensin II in solution in varying concentrations to produce the desired flow rate (700-1500 ng/kg/min) and incubated in sterile saline at 37° C. for 48 hours before implantation. Mice were induced under 2.5% isoflurane anesthesia and a 1 cm mid-scapular incision was made. The pump was inserted and closed with a wound clip or sutures.

Production of recombinant ChAT protein. Recombinant human ChAT corresponding to residue 119-748 of respective protein (EC2.3.1.6) with a N-histidine tag was expressed in E. coli BL21 (Gold) DE3 cells. When bacteria were cultured to an A600 of 0.9, IPTG (isopropyl-1-thio-beta-D-galactopyranoside) was added to a final concentration of 3 mM to induce recombinant ChAT production. Bacteria were harvested and re-suspended in cold binding buffer and sonicated at 4° C. Cells debris was removed by centrifugation and the supernatant was applied onto a high affinity Ni-charged column pre-equilibrated with binding buffer. Following sequential washings the recombinant histidine-tagged ChAT protein was eluted with 0.5 M imidazole, 10% glycerol, 20%1×DPBS. The recombinant ChAT was further purified by dialysis at 4° C. and extensive Triton X-114 extraction to remove contaminating endotoxins.

To increase the solubility and half-life of recombinant ChAT, unbranched amine-reactive MS(PEG)12 reagent (#22685, Thermo Scientific) was used to achieve the ChAT PEGylation. The reaction was performed in a buffer containing 10% glycerol, 20% DPBS 1×, 0.5 mM TCEP at a molar ratio of ChAT protein to MS(PEG)12 of 1 to 200-fold molar excess for 20 h at 4° C. Following PEGylation, the PEGylated protein was then dialyzed in buffer and further extracted with Triton X-114 to remove contaminating endotoxins.

ChAT activity assay. Activity of recombinant and PEGylated recombinant ChAT were analyzed using a colorimetric assay. ChAT and its substrates choline and acetyl-coenzyme A are incubated at 37° C. for 15 minutes. After incubation, a cocktail containing choline oxidase, 4-aminoantipyrine, phenol, and HRP is added. A red color develops in proportion to the choline remaining in the reaction mixture. By subtracting the remaining choline in wells containing ChAT from the choline remaining in a well without any enzyme, the reaction rate can be calculated.

Data Analysis. Data were analyzed using Graphpad Prism 7.0, Microsoft Excel, DSI Ponemah 6.4, and the R package "tidyverse". Statistical significance was calculated using one-way ANOVA with Tukey's correction for multiple comparisons (e.g., FIG. 1A, FIG. 6, FIG. 7B) or with paired t-tests (e.g., FIG. 8A, FIG. 8B). In all figures, $*p<0.05$; $p<0.01$; $*p<0.001$; $****p<0.0001$.

Results

Figure 1B:
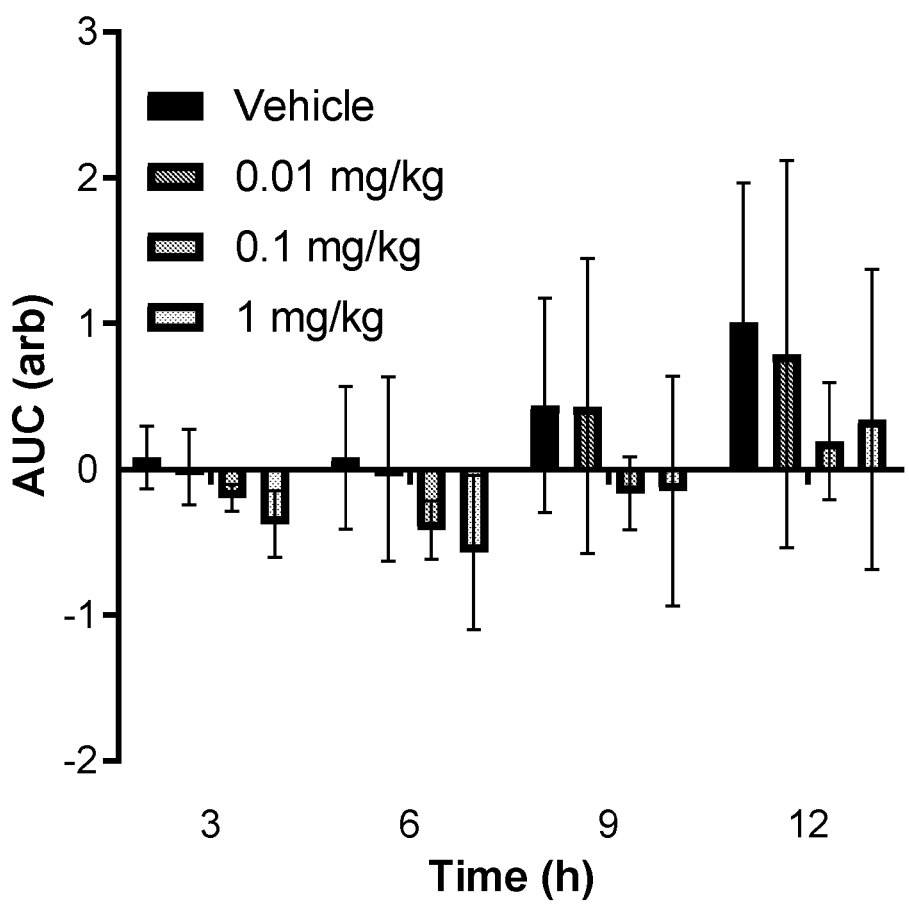
Figure 6:
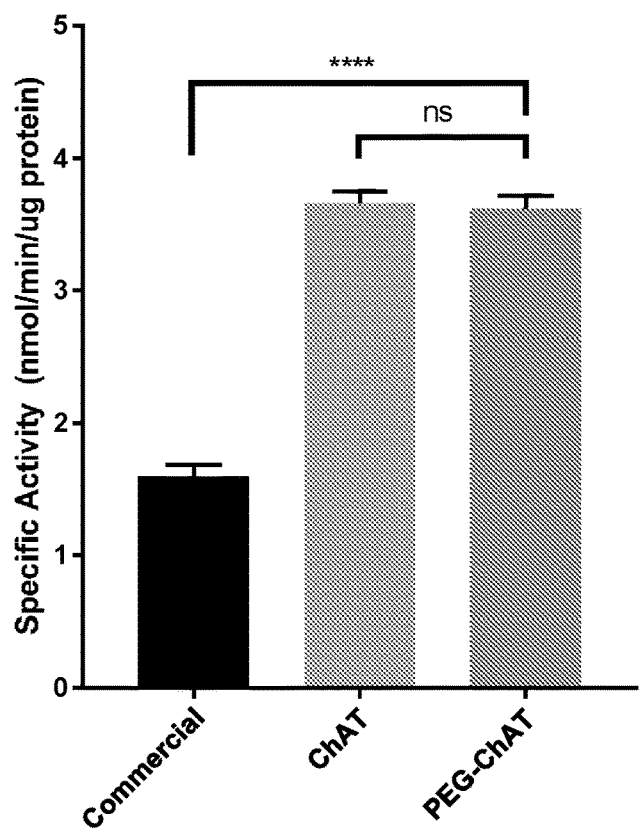
FIG. 6. PEG-ChAT retains activity after PEGylation. PEG-ChAT and rChAT exceed the specific activity of commercially available rChAT. ****$p<0.0001$.

Administration of ChAT protein decreases blood pressure. An *E. coli* expression system was used to produce recombinant ChAT protein. Isoform R of ChAT was selected. The purified protein has a molecular weight of approximately 72 kDa. A colorimetric assay was used to determine the enzymatic activity of the recombinant protein. This ChAT protein has greater than 2-fold higher specific activity than commercially available ChAT (MyBioSource MBS653740) (FIG. 6). To examine the effects of ChAT administration in a murine model of hypertension, radiotelemetry was used to accurately monitor blood pressure (BP) in awake, free-moving mice. To induce hypertension, mice were implanted with osmotic pumps delivering a constant infusion of angiotensin II (700 ng/kg/min). After inducing hypertension, mice were injected intraperitoneally (i.p.) with ChAT and blood pressure was recorded. A single injection of ChAT decreased systolic blood pressure (SBP) (FIG. 1A). The minimum SBP after ChAT injection was significantly lower than injection of vehicle control. To calculate the duration of the effect, SBP was normalized to pre-injection SBP and area-under-the-curve (AUC) was calculated. SBP was decreased for 9 hours (FIG. 1B). For 1 mg/kg ChAT group, n=5. For 0.1 mg/kg ChAT and 0.01 mg/kg ChAT groups, n=4. For vehicle group, n=11.

Chronic administration of ChAT using an osmotic pump decreases peak, average and hourly systolic blood pressure in hypertensive animals. Animals were implanted with angiotensin-II osmotic pumps to induce hypertension after collecting 3 days of baseline BP data. After implanting angiotensin-II osmotic pumps, the animals recovered for 10 days before collecting hypertensive BP data. Twenty-five days after hypertensive BP data collection, the angiotensin-II pumps were replaced with new angiotensin-II pumps. During the angiotensin-II pump replacement surgery, animals also received an additional osmotic pump containing either saline (0.9%) or ChAT solution (3.4 mg/mL, 220 ng/kg/min), n=5 both groups. After 5 days of recovery, BP data were recorded for 3 days.

Figure 2A:
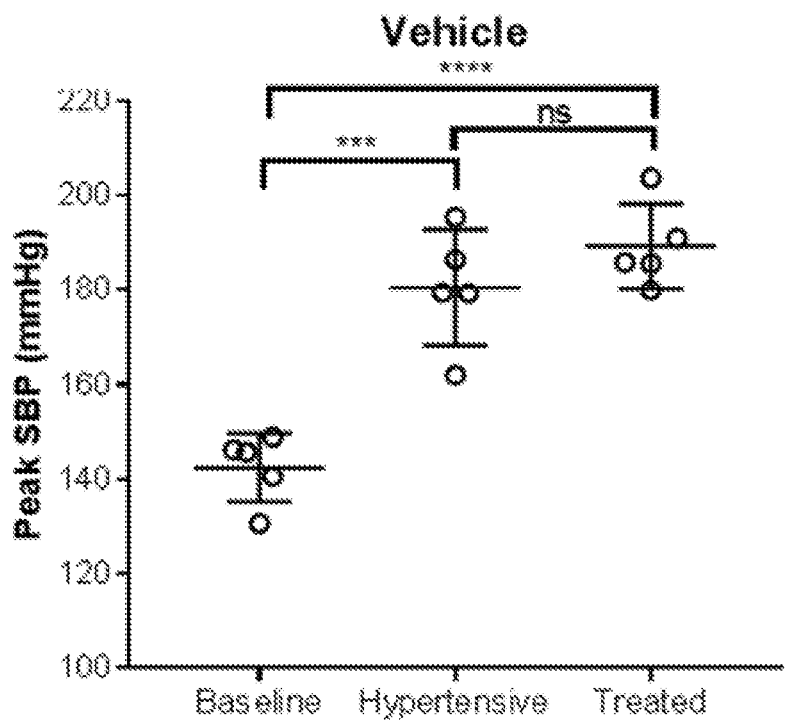
FIG. 2A-2B. Chronic administration of ChAT using an osmotic pump decreases peak systolic blood pressure (SBP) in hypertensive animals. N=5 both groups; 3 days each condition. A) Vehicle-treated animals; B) ChAT-treated animals. *$p<0.05$; $p<0.01$; *$p<0.001$; ****$p<0.0001$; ns, not significant.
Figure 2B:
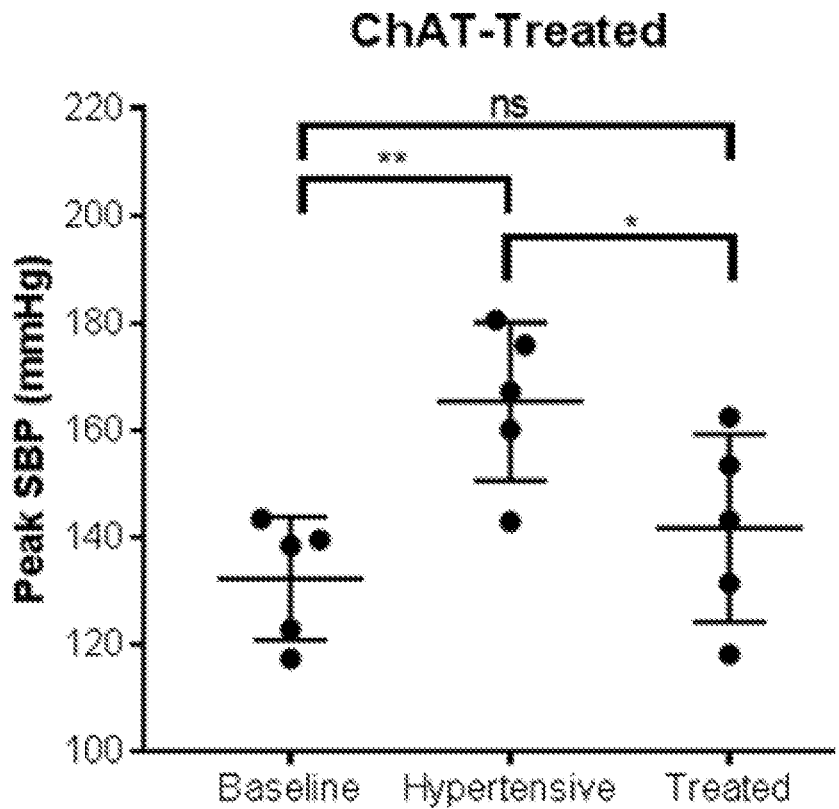
Figure 3:
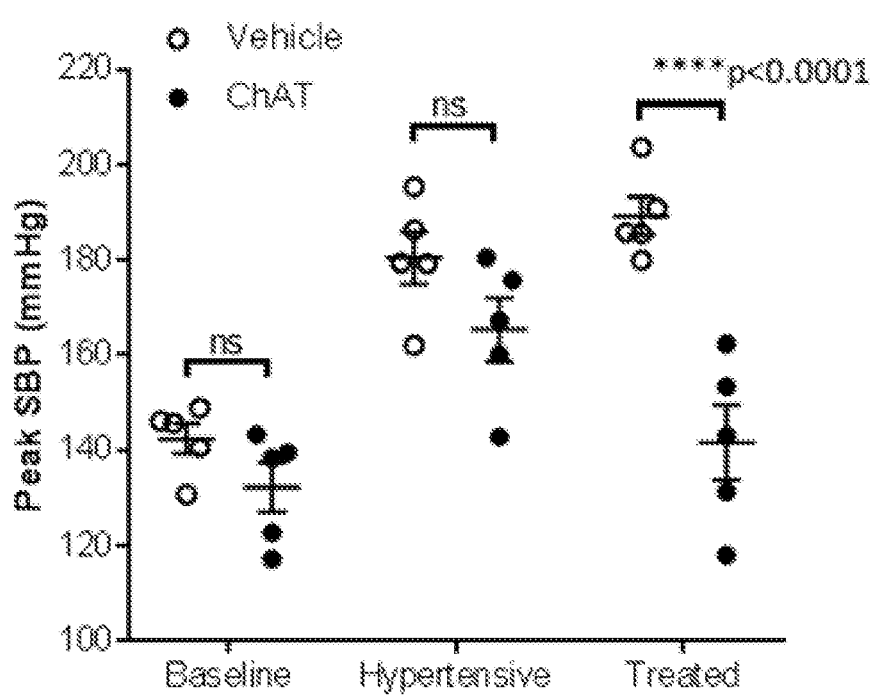
FIG. 3. Chronic administration of ChAT using an osmotic pump decreases peak systolic blood pressure in hypertensive animals. N=5 both groups; 3 days each condition.

Peak systolic blood pressure (SBP) data were recorded for 3 days in the baseline, hypertensive and treated recording period. The average data are shown in FIG. 2A-2B. Treatment with the vehicle-dispensing pump does not decrease hypertensive peak SBP (FIG. 2A). Treatment with the ChAT-dispensing pump significantly decreases hypertensive peak SBP, returning it to baseline levels (FIG. 2B). The comparison between vehicle and pump treated groups is shown in FIG. 3. During the baseline and hypertensive recording sessions, there was no difference in peak SBP between groups. During the treatment recording session, ChAT-dispensing pump treatment significantly decreased peak SBP compared to vehicle treatment. Data were analyzed using 2-way ANOVA with multiple comparisons, corrected using Tukey's test.

Figure 4A:
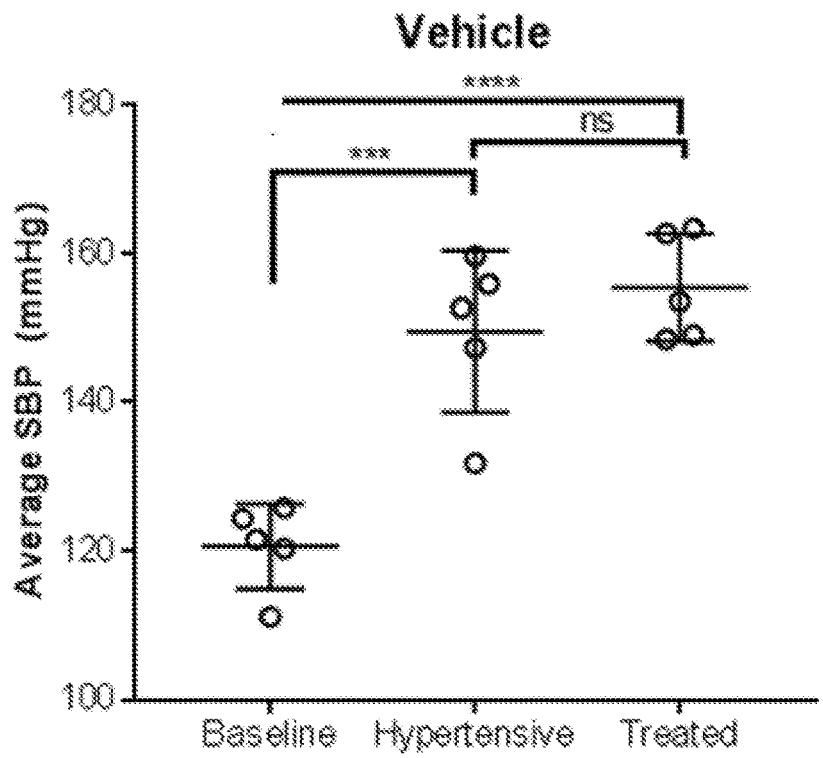
FIG. 4A-4B. Chronic administration of ChAT using an osmotic pump decreases average systolic blood pressure in hypertensive animals. N=5 both groups; 3 days each condition. A) Vehicle-treated animals; B) ChAT-treated animals. *$p<0.05$, $p<0.01$, *$p<0.001$, ****$p<0.0001$.
Figure 4B:
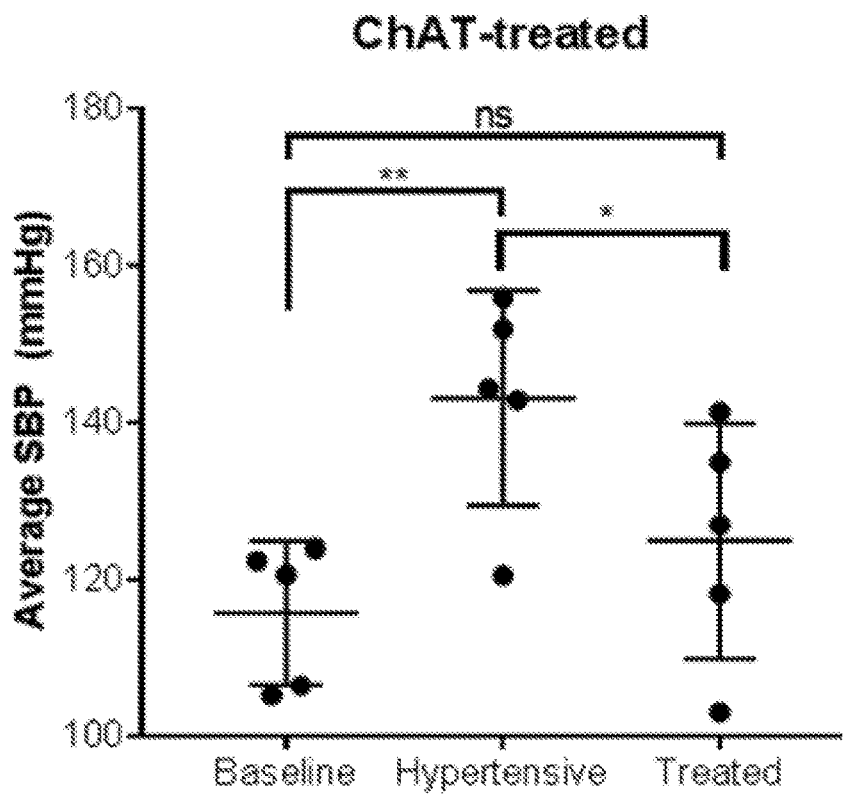
Figure 5:
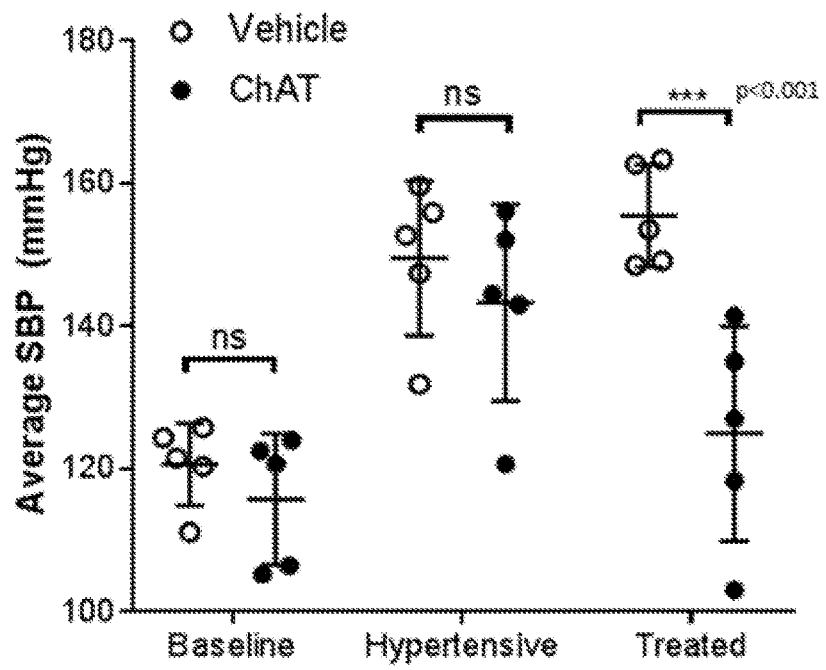
FIG. 5. Chronic administration of ChAT using an osmotic pump decreases average systolic blood pressure in hypertensive animals. N=5 both groups; 3 days each condition.

Chronic administration of ChAT using an osmotic pump decreases average SBP in hypertensive animals (FIG. 4A-4B). SBP was averaged over the 72 hours during each recording session. Treatment with the vehicle-dispensing pump does not decrease hypertensive average SBP (FIG. 4A). Treatment with the ChAT-dispensing pump significantly decreases hypertensive average SBP, returning it to baseline levels (FIG. 4B). The comparison between vehicle and pump treated groups is shown in FIG. 5. During the baseline and hypertensive recording sessions, there was no difference in average SBP between groups. During the treatment recording session, ChAT-dispensing pump treatment significantly decreases average SBP compared to vehicle treatment. Data were analyzed using 2-way ANOVA with multiple comparisons, corrected using Tukey's test. Chronic administration of ChAT using an osmotic pump also decreases hourly systolic BP.

Figure 7A:
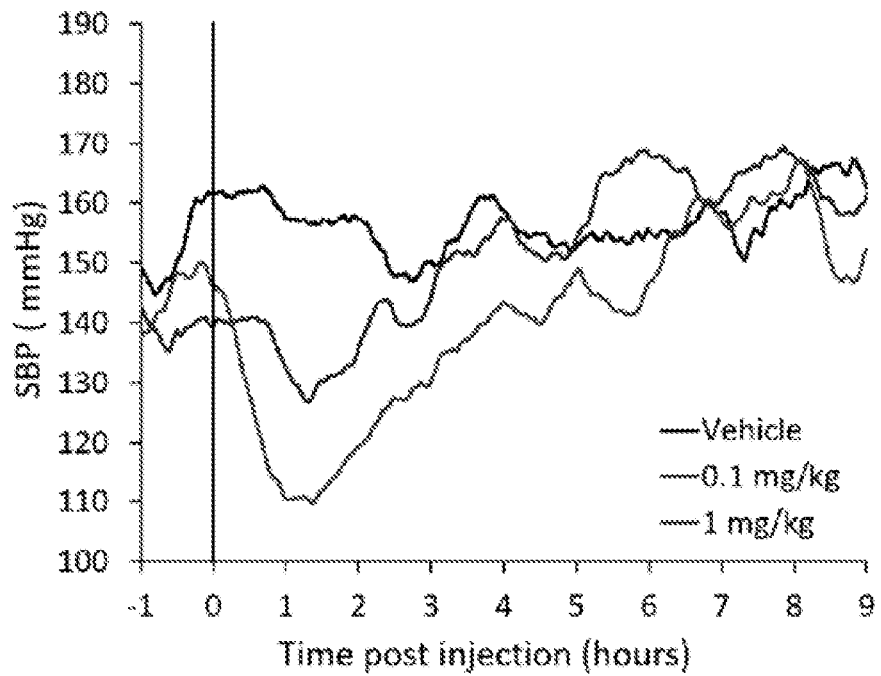
FIG. 7A-7D. A single injection of PEG-ChAT decreases systolic blood pressure (SBP) in hypertensive mice. A) PEG-ChAT was injected IP at the indicated doses at the black vertical line (time 0). For PEG-ChAT 1 mg/kg and 0.1 mg/kg, n=7. For vehicle, n=5. Traces from top to bottom at 1 hour post injection: vehicle, 0.1 mg/kg, 1 mg/kg. B) Minimum SBP during 12 hour post-injection period. C) Normotensive-normalized SBP during 12 hour post-injection period. Traces from top to bottom at 1 hour post injection: vehicle, 0.1 mg/kg, 1 mg/kg. D) Area-under-curve of hypertensive-normalized SBP during 12 hour post-injection period. For 1 mg/kg PEG-ChAT group, n=7. For 0.1 mg/kg PEG-ChAT group, n=7. For vehicle group, n=11. $p<0.01$; *$p<0.001$.
Figure 7B:
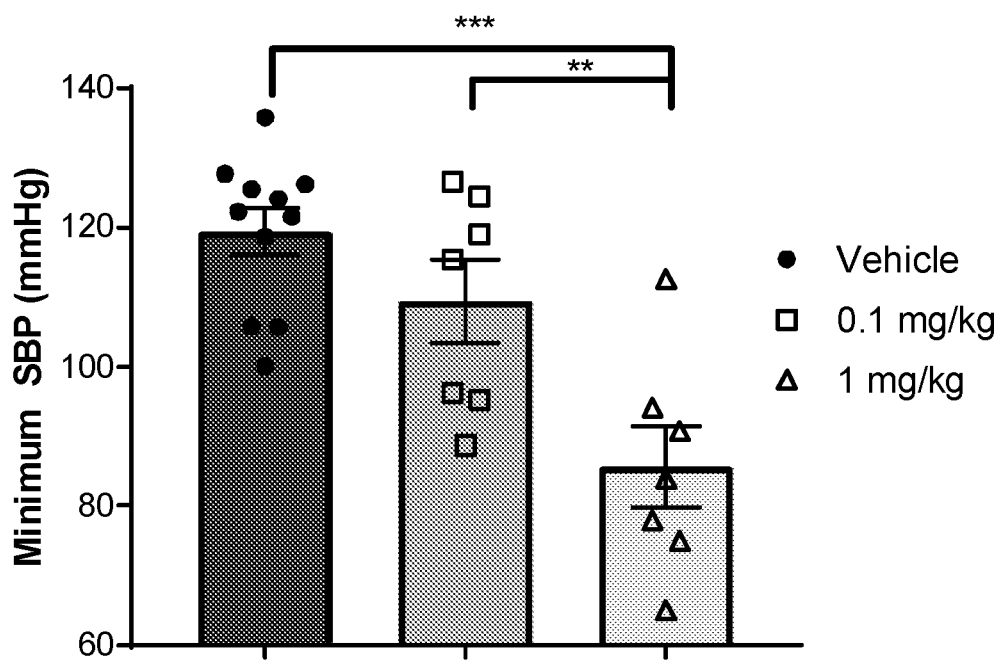
Figure 7C:
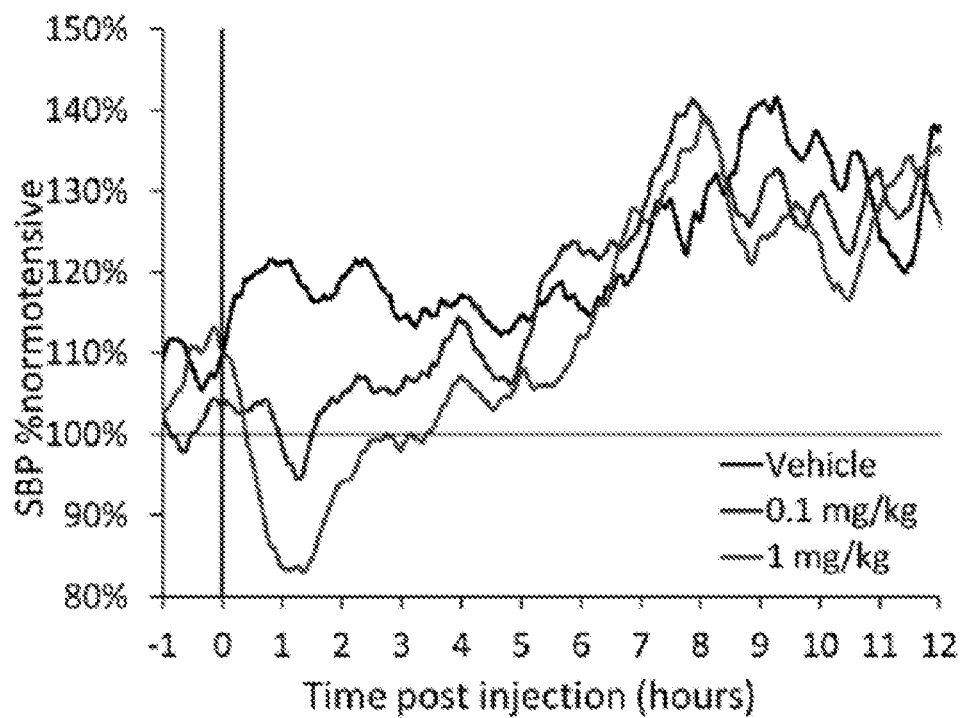
Figure 7D:
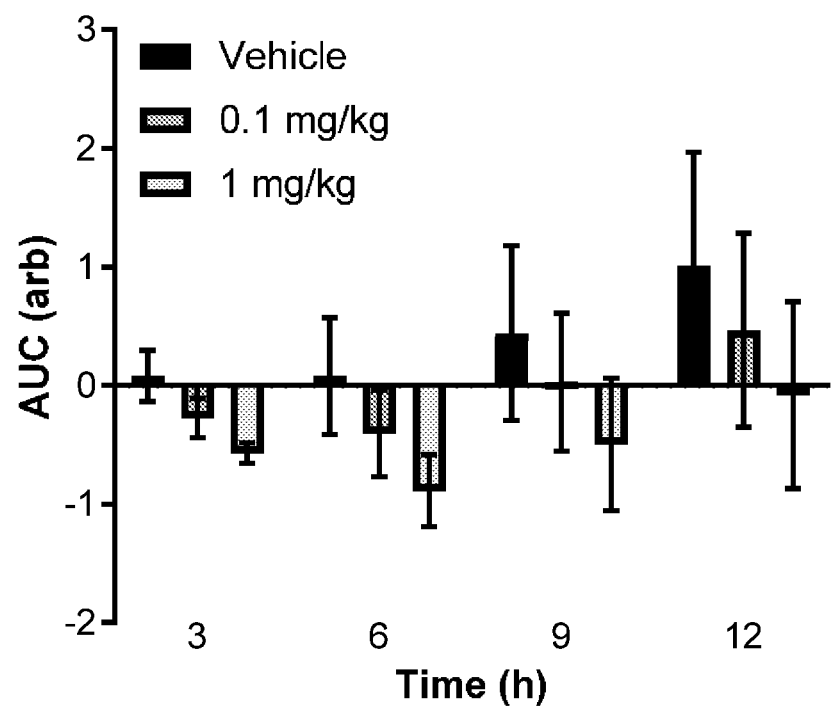

PEGylated ChAT leads to greater reductions in blood pressure than rChAT. To increase the duration of the effect of recombinant ChAT administration, ChAT was PEGylated to create PEGylated recombinant ChAT (PEG-ChAT). PEGylation increases hydrodynamic radius and immunogenicity, leading to more durable biologic molecules with longer lasting biological effects. The molecular weight of PEG-ChAT was approximately 95 kDa, a ~20 kD increase compared to rChAT. PEG-ChAT has comparable specific activity to rChAT, which is significantly higher than commercially available rChAT (FIG. 6). After inducing hypertension, mice were injected i.p. with PEG-ChAT. A single injection of PEG-ChAT produces decreases in blood pressure in a dose-dependent manner (FIG. 7A-7B). A single PEG-ChAT injection was able to decrease SBP to normotensive levels despite the animals being hypertensive before injection (FIG. 7C), and area-under-the-curve analysis again normalized to hypertensive SBP showed a duration of effect of 12 hours (FIG. 7D). For 1 mg/kg PEG-ChAT group, n=7. For 0.1 mg/kg PEG-ChAT group, n=7. For vehicle group, n=11.

Figure 8A:
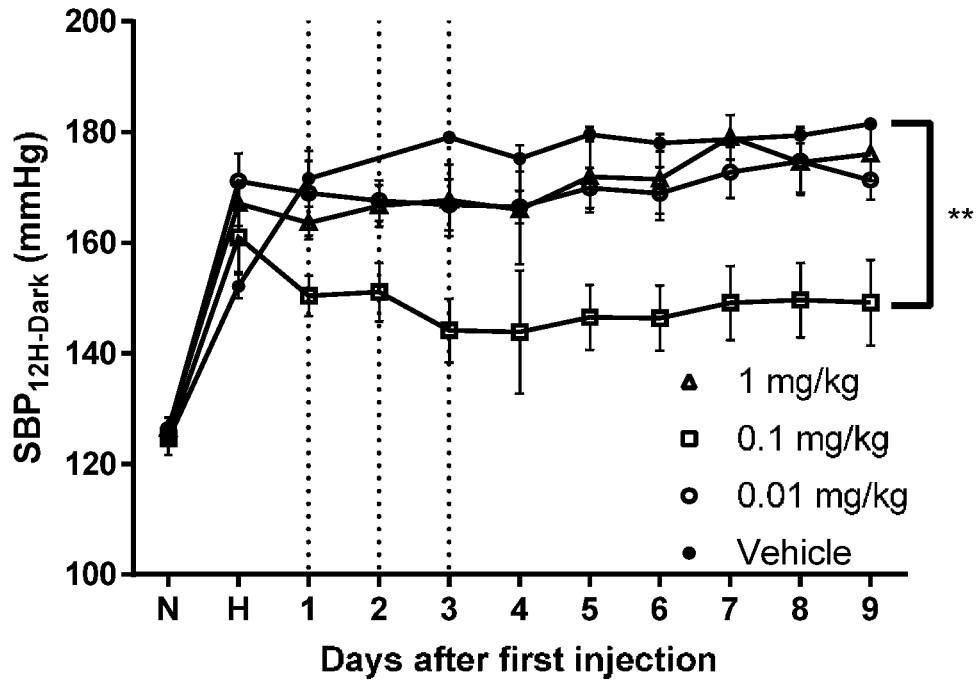
FIG. 8A-8B. Daily doses of PEG-ChAT reduce SBP in hypertensive mice. A) SBP averaged during the active cycle for nocturnal mice ($SBP_{12H\text{-}Dark}$) while normotensive, hypertensive, or post-PEG-ChAT injection. N; normotensive. H; hypertensive. The first injection occurred on day 1, and injections are represented by vertical dotted lines. Injections occurred on days 1, 2, and 3. B) Hypertensive index of mice during and after PEG-ChAT injections. To calculate the hypertensive index, first SBP is normalized to normotensive SBP. The AUC of this hypertensive-normalized SBP for a single day is calculated from a baseline of 1 ("AUC24"). The AUC24 is divided by AUC24-Hypertensive to generate the hypertensive index. A hypertensive index of 1 is equivalent to typical angiotensin II-induced hypertension as recorded before injections. A hypertensive index of 0 is normotensive as recorded before angiotensin II osmotic pump implant. Daily doses of 0.1 mg/kg PEG-ChAT produced a persistently lowered hypertensive index. For PEG-ChAT 1 mg/kg group, n=7; for PEG-ChAT 0.1 mg/kg group, n=9; for PEG-ChAT 0.01 mg/kg group, n=6; for vehicle group, n=2. p<0.01; *p<0.001; ****p<0.0001.
Figure 8B:
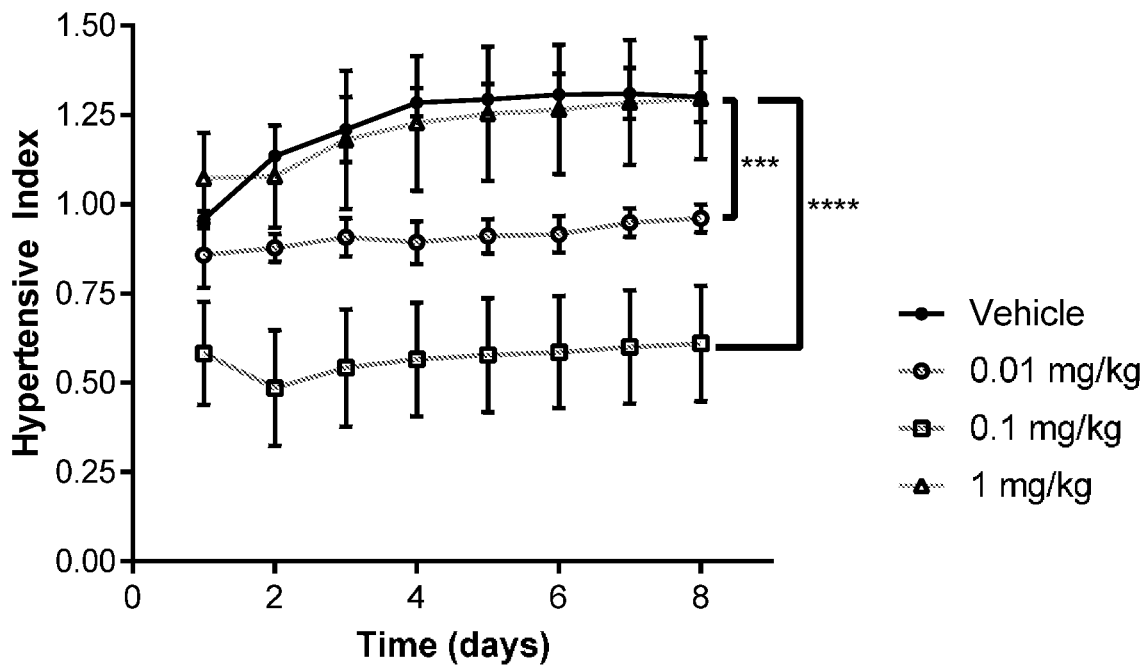

Repeated doses of PEGylated ChAT lead to long-lasting effects. Since a single dose of PEG-ChAT produced larger decreases in blood pressure than rChAT, the duration of this effect was increased by injecting PEG-ChAT once per day for multiple consecutive days utilizing the same hypertension model. Normotensive and hypertensive SBP were measured for all animals before injections. SBP was averaged during the period when room lights are off ($SBP_{12H\text{-}Dark}$), as that is the active cycle for nocturnal mice. Multiple injections of PEG-ChAT significantly decreased SBP $SBP_{12H\text{-}Dark}$ for a week post-injection (FIG. 8A). SBP was normalized to normotensive SBP and averaged hourly, showing that injections of 0.1 mg/kg could decrease SBP close to normotensive levels. To further characterize the decrease in blood pressure, a "hypertensive index" was developed for the murine hypertension model. To calculate the hypertensive index, first systolic blood pressure (SBP), recorded after angiotensin II pump implant but before injections, was normalized to normotensive SBP. The area under the curve (AUC) of this normotensive-normalized SBP for a single day was calculated from a baseline of 1 ("AUC24-Hypertensive"). This AUC24-Hypertensive value is an indication of the severity of hypertension and is dependent on the response to angiotensin II infusion. Calculating this value allows for the elimination of differential responses to angiotensin II between experimental groups. SBP recorded during and after injections is also normalized to normotensive SBP. The AUC of this normotensive-normalized SBP for a single day is calculated from a baseline of 1 ("AUC24"). The AUC24 is divided by AUC24-Hypertensive to generate the hypertensive index. A hypertensive index of 1 is equivalent to typical angiotensin II-induced hypertension as recorded before injections. A hypertensive index of 0 is normotensive as recorded before angiotensin II osmotic pump implant. Daily doses of 0.01 and 0.1 mg/kg PEG-ChAT produced a persistently lowered hypertensive index, with 0.1 mg/kg PEG-ChAT doses having a greater effect (FIG. 8B). For 1 mg/kg PEG-ChAT group, n=7. For 0.1 mg/kg PEG-ChAT group, n=9. For 0.01 mg/kg PEG-ChAT group, n=5. For vehicle group, n=2.

REFERENCES

Centers for Disease Control and Prevention (CDC) High Blood Pressure Fact Sheet, world wide web cdc.gov/dhdsp/data_statistics/fact_sheets/fs_bloodpressure.htm, Jul. 16, 2016.

Fu A L, Huang S J, Sun M J. Complementary remedy of aged-related learning and memory deficits via exogenous choline acetyltransferase. Biochem Biophys Res Commun. 2005 Oct. 14; 336(1):268-73.

PCT International Patent Application Publication No. WO 2005/071071 A1, published Aug. 4, 2005, PTD-Human Choline Acetyltransferase Fusion Protein and its Application, Institute of Pharmacology and Toxicology, Academy of Military Medical Sciences P.L.A. China.

U.S. Pat. No. 9,248,152 B2, issued Feb. 2, 2016, Human Neural Stem Cells Expressing Human Choline Acetyltransferase, and Use Thereof, Kim et al.

U.S. Pat. No. 7,083,930 B2, issued Aug. 1, 2006, Human Choline Acetyltransferase, Hudson et al.

What is claimed is:

1. A method of reducing systemic hypertension in a subject in need thereof comprising administering to the subject a choline acetyltransferase (ChAT) protein or a ChAT protein conjugated to polyethylene glycol (PEG) in an amount and manner effective to reduce systemic hypertension in a subject,
   wherein the subject is an adult human 18 years or older who prior to administration of ChAT protein or PEGylated ChAT protein had a resting systolic blood pressure at or above 130 mmHg and/or a diastolic blood pressure at or above 80 mmHg, and
   wherein administration of ChAT protein or PEGylated ChAT protein is effective to reduce systolic blood pressure by 10-40 mmHg.

2. The method of claim 1, wherein ChAT protein is conjugated to polyethylene glycol (PEG).

3. The method of claim 2, wherein ChAT protein is conjugated to 2-24 PEG chains.

4. The method of claim 2, wherein ChAT protein is conjugated to 12 PEG chains.

5. The method of claim 2, wherein each PEG chain has a molecular weight of 200-2,000 daltons.

6. The method of claim 1, wherein the subject is an adult human 18 years or older who prior to administration of ChAT protein or PEGylated ChAT protein had a resting systolic blood pressure at or above 140 mmHg and/or a diastolic blood pressure at or above 90 mmHg.

7. The method of claim 1, wherein the subject has primary hypertension.

8. The method of claim 1, wherein the subject has secondary hypertension.

9. The method of claim 8, wherein the subject has narrowing of the arteries and/or chronic kidney disease.

10. The method of claim 1, wherein ChAT protein or PEGylated ChAT protein is administered by intravenous or intraperitoneal injection or via a pump.

11. The method of claim 1, wherein ChAT protein or PEGylated ChAT protein is administered by injections or infusions spaced over an interval of one or more days.

12. The method of claim 1, wherein ChAT protein or PEGylated ChAT protein is chronically administered via a pump.

13. The method of claim 1, wherein administration of ChAT protein or PEGylated ChAT protein is effective to reduce systolic blood pressure by at least 10 mmHg.

14. The method of claim 1, wherein administration of ChAT protein or PEGylated ChAT protein is effective to reduce systolic blood pressure by at least 20 mmHg.

15. The method of claim 1, wherein administration of ChAT protein or PEGylated ChAT protein is effective to reduce systolic blood pressure by at least 30 mmHg.

16. The method of claim 1, wherein ChAT protein or PEGylated ChAT protein is human recombinant ChAT protein.

17. The method of claim 1, wherein ChAT protein or PEGylated ChAT protein is ChAT protein isoform R.

18. The method of claim 1, wherein the subject does not have any one or more of an age-related cognitive disorder, Alzheimer's disease, a neurodegenerative disease, amyotrophic lateral sclerosis, senile dementia, multi-infarct dementia, familial dysautonomia, Huntington's disease, mental retardation, memory loss, myasthenia gravis, a gastrointestinal tract disorder, a spinal cord disorder, a brainstem disorders, a hypothalamic disorder, a limbic system disorder and dementia.

\* \* \* \* \*

SEQUENCE LISTING

```
<160> NUMBER OF SEQ ID NOS: 2

<210> SEQ ID NO 1
<211> LENGTH: 748
<212> TYPE: PRT
<213> ORGANISM: Homo sapiens

<400> SEQUENCE: 1

Met Gly Leu Arg Thr Ala Lys Lys Arg Gly Leu Gly Gly Gly Gly Lys
1               5                   10                  15

Trp Lys Arg Glu Glu Gly Gly Thr Arg Gly Arg Arg Glu Val Arg
                20                  25                  30

Pro Ala Cys Phe Leu Gln Ser Gly Gly Arg Gly Asp Pro Gly Asp Val
            35                  40                  45

Gly Gly Pro Ala Gly Asn Pro Gly Cys Ser Pro His Pro Arg Ala Ala
        50                  55                  60

Thr Arg Pro Pro Pro Leu Pro Ala His Thr Pro Ala His Thr Pro Glu
65                  70                  75                  80

Trp Cys Gly Ala Ala Ser Ala Glu Ala Ala Glu Pro Arg Arg Ala Gly
                85                  90                  95

Pro His Leu Cys Ile Pro Ala Pro Gly Leu Thr Lys Thr Pro Ile Leu
            100                 105                 110

Glu Lys Val Pro Arg Lys Met Ala Ala Lys Thr Pro Ser Ser Glu Glu
        115                 120                 125

Ser Gly Leu Pro Lys Leu Pro Val Pro Pro Leu Gln Gln Thr Leu Ala
    130                 135                 140

Thr Tyr Leu Gln Cys Met Arg His Leu Val Ser Glu Glu Gln Phe Arg
145                 150                 155                 160

Lys Ser Gln Ala Ile Val Gln Gln Phe Gly Ala Pro Gly Gly Leu Gly
                165                 170                 175

Glu Thr Leu Gln Gln Lys Leu Leu Glu Arg Gln Glu Lys Thr Ala Asn
            180                 185                 190

Trp Val Ser Glu Tyr Trp Leu Asn Asp Met Tyr Leu Asn Asn Arg Leu
        195                 200                 205

Ala Leu Pro Val Asn Ser Ser Pro Ala Val Ile Phe Ala Arg Gln His
    210                 215                 220

Phe Pro Gly Thr Asp Asp Gln Leu Arg Phe Ala Ala Ser Leu Ile Ser
225                 230                 235                 240

Gly Val Leu Ser Tyr Lys Ala Leu Leu Asp Ser His Ser Ile Pro Thr
                245                 250                 255

Asp Cys Ala Lys Pro Glu Leu Ser Gly Gln Pro Leu Cys Met Lys Gln
```

```
                260                 265                 270
Tyr Tyr Gly Leu Phe Ser Ser Tyr Arg Leu Pro Gly His Thr Gln Asp
            275                 280                 285
Thr Leu Val Ala Gln Asn Ser Ser Ile Met Pro Glu Pro Glu His Val
        290                 295                 300
Ile Val Ala Cys Cys Asn Gln Phe Phe Val Leu Asp Val Val Ile Asn
    305                 310                 315                 320
Phe Arg Arg Leu Ser Glu Gly Asp Leu Phe Thr Gln Leu Arg Lys Ile
                325                 330                 335
Val Lys Met Ala Ser Asn Glu Asp Glu Arg Leu Pro Pro Ile Gly Leu
            340                 345                 350
Leu Thr Ser Asp Gly Arg Ser Glu Trp Ala Glu Ala Arg Thr Val Leu
        355                 360                 365
Val Lys Asp Ser Thr Asn Arg Asp Ser Leu Asp Met Ile Glu Arg Cys
    370                 375                 380
Ile Cys Leu Val Cys Leu Asp Gly Pro Gly Gly Val Glu Leu Ser Asp
385                 390                 395                 400
Thr His Arg Ala Leu Gln Leu Leu His Gly Gly Tyr Ser Lys Asn
                405                 410                 415
Gly Ala Asn Arg Trp Tyr Asp Lys Ser Leu Gln Phe Val Val Gly Arg
            420                 425                 430
Asp Ala Thr Cys Gly Val Val Cys Glu His Ser Pro Phe Asp Gly Ile
        435                 440                 445
Val Leu Val Gln Cys Thr Glu His Leu Leu Lys His Met Thr Gln Ser
    450                 455                 460
Ser Arg Lys Leu Ile Arg Ala Asp Ser Val Ser Glu Leu Pro Ala Pro
465                 470                 475                 480
Arg Arg Leu Arg Trp Lys Cys Ser Pro Glu Ile Gln Gly His Leu Ala
                485                 490                 495
Ser Ser Ala Glu Lys Leu Gln Arg Ile Val Lys Asn Leu Asp Phe Ile
            500                 505                 510
Val Tyr Lys Phe Asp Asn Tyr Gly Lys Thr Phe Ile Lys Lys Gln Lys
        515                 520                 525
Cys Ser Pro Asp Ala Phe Ile Gln Val Ala Leu Gln Leu Ala Phe Tyr
    530                 535                 540
Arg Leu His Arg Arg Leu Val Pro Thr Tyr Glu Ser Ala Ser Ile Arg
545                 550                 555                 560
Arg Phe Gln Glu Gly Arg Val Asp Asn Ile Arg Ser Ala Thr Pro Glu
                565                 570                 575
Ala Leu Ala Phe Val Arg Ala Val Thr Asp His Lys Ala Ala Val Pro
            580                 585                 590
Ala Ser Glu Lys Leu Leu Leu Lys Asp Ala Ile Arg Ala Gln Thr
        595                 600                 605
Ala Tyr Thr Val Met Ala Ile Thr Gly Met Ala Ile Asp Asn His Leu
    610                 615                 620
Leu Ala Leu Arg Glu Leu Ala Arg Ala Met Cys Lys Glu Leu Pro Glu
625                 630                 635                 640
Met Phe Met Asp Glu Thr Tyr Leu Met Ser Asn Arg Phe Val Leu Ser
                645                 650                 655
Thr Ser Gln Val Pro Thr Thr Thr Glu Met Phe Cys Cys Tyr Gly Pro
            660                 665                 670
Val Val Pro Asn Gly Tyr Gly Ala Cys Tyr Asn Pro Gln Pro Glu Thr
        675                 680                 685
```

-continued

```
Ile Leu Phe Cys Ile Ser Ser Phe His Ser Cys Lys Glu Thr Ser Ser
    690             695                 700

Ser Lys Phe Ala Lys Ala Val Glu Glu Ser Leu Ile Asp Met Arg Asp
705             710                 715                 720

Leu Cys Ser Leu Leu Pro Pro Thr Glu Ser Lys Pro Leu Ala Thr Lys
                725                 730                 735

Glu Lys Ala Thr Arg Pro Ser Gln Gly His Gln Pro
            740                 745

<210> SEQ ID NO 2
<211> LENGTH: 630
<212> TYPE: PRT
<213> ORGANISM: Homo sapiens

<400> SEQUENCE: 2

Met Ala Ala Lys Thr Pro Ser Ser Glu Glu Ser Gly Leu Pro Lys Leu
1               5                   10                  15

Pro Val Pro Pro Leu Gln Gln Thr Leu Ala Thr Tyr Leu Gln Cys Met
                20                  25                  30

Arg His Leu Val Ser Glu Glu Gln Phe Arg Lys Ser Gln Ala Ile Val
            35                  40                  45

Gln Gln Phe Gly Ala Pro Gly Gly Leu Gly Glu Thr Leu Gln Gln Lys
    50                  55                  60

Leu Leu Glu Arg Gln Glu Lys Thr Ala Asn Trp Val Ser Glu Tyr Trp
65                  70                  75                  80

Leu Asn Asp Met Tyr Leu Asn Asn Arg Leu Ala Leu Pro Val Asn Ser
                85                  90                  95

Ser Pro Ala Val Ile Phe Ala Arg Gln His Phe Pro Gly Thr Asp Asp
                100                 105                 110

Gln Leu Arg Phe Ala Ala Ser Leu Ile Ser Gly Val Leu Ser Tyr Lys
            115                 120                 125

Ala Leu Leu Asp Ser His Ser Ile Pro Thr Asp Cys Ala Lys Gly Gln
    130                 135                 140

Leu Ser Gly Gln Pro Leu Cys Met Lys Gln Tyr Tyr Gly Leu Phe Ser
145                 150                 155                 160

Ser Tyr Arg Leu Pro Gly His Thr Gln Asp Thr Leu Val Ala Gln Asn
                165                 170                 175

Ser Ser Ile Met Pro Glu Pro Glu His Val Ile Val Ala Cys Cys Asn
                180                 185                 190

Gln Phe Phe Val Leu Asp Val Val Ile Asn Phe Arg Arg Leu Ser Glu
            195                 200                 205

Gly Asp Leu Phe Thr Gln Leu Arg Lys Ile Val Lys Met Ala Ser Asn
    210                 215                 220

Glu Asp Glu Arg Leu Pro Pro Ile Gly Leu Leu Thr Ser Asp Gly Arg
225                 230                 235                 240

Ser Glu Trp Ala Glu Ala Arg Thr Val Leu Val Lys Asp Ser Thr Asn
                245                 250                 255

Arg Asp Ser Leu Asp Met Ile Glu Arg Cys Ile Cys Leu Val Cys Leu
                260                 265                 270

Asp Ala Pro Gly Gly Val Glu Leu Ser Asp Thr His Arg Ala Leu Gln
            275                 280                 285

Leu Leu His Gly Gly Gly Tyr Ser Lys Asn Gly Ala Asn Arg Trp Tyr
    290                 295                 300

Asp Lys Ser Leu Gln Phe Val Val Gly Arg Asp Gly Thr Cys Gly Val
```

-continued

```
305                 310                 315                 320
Val Cys Glu His Ser Pro Phe Asp Gly Ile Val Leu Val Gln Cys Thr
            325                 330                 335

Glu His Leu Leu Lys His Met Thr Gln Ser Ser Arg Lys Leu Ile Arg
            340                 345                 350

Ala Asp Ser Val Ser Glu Leu Pro Ala Pro Arg Arg Leu Arg Trp Lys
            355                 360                 365

Cys Ser Pro Glu Ile Gln Gly His Leu Ala Ser Ala Glu Lys Leu
            370                 375                 380

Gln Arg Ile Val Lys Asn Leu Asp Phe Ile Val Tyr Lys Phe Asp Asn
385             390                 395                 400

Tyr Gly Lys Thr Phe Ile Lys Lys Gln Lys Cys Ser Pro Asp Ala Phe
                405                 410                 415

Ile Gln Val Ala Leu Gln Leu Ala Phe Tyr Arg Leu His Arg Arg Leu
            420                 425                 430

Val Pro Thr Tyr Glu Ser Ala Ser Ile Arg Arg Phe Gln Glu Gly Arg
            435                 440                 445

Val Asp Asn Ile Arg Ser Ala Thr Pro Glu Ala Leu Ala Phe Val Arg
450             455                 460

Ala Val Thr Asp His Lys Ala Ala Val Pro Ala Ser Glu Lys Leu Leu
465             470                 475                 480

Leu Leu Lys Asp Ala Ile Arg Ala Gln Thr Ala Tyr Thr Val Met Ala
            485                 490                 495

Ile Thr Gly Met Ala Ile Asp Asn His Leu Leu Ala Leu Arg Glu Leu
            500                 505                 510

Ala Arg Ala Met Cys Lys Glu Leu Pro Glu Met Phe Met Asp Glu Thr
            515                 520                 525

Tyr Leu Met Ser Asn Arg Phe Val Leu Ser Thr Ser Gln Val Pro Thr
            530                 535                 540

Thr Thr Glu Met Phe Cys Cys Tyr Gly Pro Val Val Pro Asn Gly Tyr
545                 550                 555                 560

Gly Ala Cys Tyr Asn Pro Gln Pro Glu Thr Ile Leu Phe Cys Ile Ser
                565                 570                 575

Ser Phe His Ser Cys Lys Glu Thr Ser Ser Ser Lys Phe Ala Lys Ala
            580                 585                 590

Val Glu Glu Ser Leu Ile Asp Met Arg Asp Leu Cys Ser Leu Leu Pro
            595                 600                 605

Pro Thr Glu Ser Lys Pro Leu Ala Thr Lys Glu Lys Ala Thr Arg Pro
    610                 615                 620

Ser Gln Gly His Gln Pro
625                 630
```